United States Patent [19]
Spillert et al.

[11] Patent Number: 4,814,247
[45] Date of Patent: * Mar. 21, 1989

[54] METHOD FOR DETERMINING THE EXISTANCE AND/OR THE MONITORING OF A PATHOLOGICAL CONDITION IN A MAMMAL

[75] Inventors: Charles R. Spillert, West Orange; William A. Suval, Liberty Corners; Eric J. Lazaro, Jersey City, all of N.J.

[73] Assignee: University of Medicine and Dentistry of New Jersey, Newark, N.J.

[*] Notice: The portion of the term of this patent subsequent to Nov. 10, 2004 has been disclaimed.

[21] Appl. No.: 34,101

[22] PCT Filed: May 16, 1986

[86] PCT No.: PCT/US86/01075
§ 371 Date: Mar. 16, 1987
§ 102(e) Date: Mar. 16, 1987

[87] PCT Pub. No.: WO86/06840
PCT Pub. Date: Nov. 20, 1986

Related U.S. Application Data

[63] Continuation-in-part of Ser. No. 734,799, May 16, 1985, Pat. No. 4,705,756, which is a continuation-in-part of Ser. No. 703,120, Feb. 19, 1985, abandoned, which is a continuation of Ser. No. 538,783, Oct. 4, 1983, abandoned, which is a continuation-in-part of Ser. No. 440,540, Jan. 26, 1983, abandoned.

[51] Int. Cl.⁴ ............................................. G01N 33/86
[52] U.S. Cl. ....................................... 436/69; 436/64; 435/13; 422/61; 422/73
[58] Field of Search ................... 422/61, 73; 435/4, 7, 435/13, 29, 34, 39, 810; 436/64, 69, 813

[56] References Cited

U.S. PATENT DOCUMENTS

| 3,267,364 | 6/1966 | Page et al. ...................... 436/69 X |
| 3,449,081 | 6/1969 | Hughes ................................ 422/61 |
| 3,541,202 | 11/1970 | Meyer et al. ..................... 435/13 X |
| 3,792,044 | 2/1974 | Dooley ................................ 436/95 |
| 4,038,147 | 7/1977 | Reno ................................... 435/13 |
| 4,047,890 | 9/1977 | Eichelberger et al. ............. 436/69 |
| 4,210,622 | 7/1980 | Soothill et al. ..................... 422/61 |
| 4,289,498 | 9/1981 | Baughman et al. ............ 436/69 X |
| 4,705,756 | 5/1985 | Spillert et al. ....................... 436/69 |

FOREIGN PATENT DOCUMENTS 595996  3/1982  U.S.S.R. ................................. 435/4

OTHER PUBLICATIONS

Osterud, B., et als., SCAND. J. HAEMATOL, (1982) 29, pp. 175–184.
Dintenfass et al; Effect of Fibrinogen on Aggregation of Red Cells; Microvasc. Res., 9 (1) 107–118, 1975.
Ishikawa et al; Effect of Heparinized Blood Exchange Transfusion; Abstract, Medline File, Index Medicus subfile (80051517) 1979.
Dale et al; Intravascular Hemolysis; Abstract, Medline File, Index Medicus subfile, (80224783) 1980.

Primary Examiner—Barry S. Richman
Assistant Examiner—Lyle Alfandary-Alexander
Attorney, Agent, or Firm—Klauber & Jackson

[57] ABSTRACT

There is disclosed a method of testing a cellular hematologic fluid derived from a mammal to determine the existence in the mammal of a pathological state or condition wherein an immunomodulator is admixed with the cellular hematologic fluid of the mammal and a reaction parameter determined and compared with known reaction parameters of cellular hematologic fluids of mammals of known healthy states to like immunomodulator. In a preferred embodiment of the present invention, the reaction parameter is a clotting parameter as determined as fibrin levels.

20 Claims, No Drawings

METHOD FOR DETERMINING THE EXISTANCE AND/OR THE MONITORING OF A PATHOLOGICAL CONDITION IN A MAMMAL

RELATED APPLICATIONS

This is a continuation-in-part application of U.S. application Ser. No. 734,799, filed May 16, 1985, now U.S. Pat. No. 4,705,756 issued Nov. 10, 1987, which is in turn a continuation-in-part of U.S. application Ser. No. 703,120, filed Feb. 19, 1985, now abandoned which is a continuation application of U.S. application Ser. No. 06/538,783, filed Oct. 4, 1983, now abandoned, which is continuation-in-part application of U.S. application Ser. No. 06/440,540, filed January 26, 1983, now abandoned.

FIELD OF THE INVENTION

This invention relates to a method of testing a hematologic fluid, and more particularly to a method of testing to determine the existence in the mammal of a pathological state or condition, to monitor a known pathological state existing in a mammal and a test kit therefor.

DESCRIPTION OF THE PRIOR ART

Common diagnostic tests performed on asymptomatic individuals during the course of their annual physical examiniation might include: complete blood count (CBC), blood chemistries (e.g. glucose or electrolyte levels) and urinalysis (test for glucose, ketones, etc.). Occasionally, these tests may detect a disease which was not obvious upon physical examination alone. These routine screening test would be useless in detecting at an early stage the disease states which kill and disable the great majority of individuals including cancer, rheumatic diseases, AIDS, heart disease, vascular disease, and others. Such disease states can in part be characterized by abnormalities in either the blood coagulation or immune response system, or both.

At present, the detection in a mammal of a pathological state or condition, e.g. cancer, AIDS, sepsis and the like is generally performed after the mammal has experienced some abnormal physical response, e.g. lack of energy, headaches, rectal bleeding, lumps, etc., or as preliminarily detected during an annual physical examination. Once evidencing such abnormal physical response, diagnostic procedures and/or other protocols are thereafter initiated and evaluated to qualify the pathological state as well as to quantify the extent of advancement of the pathological state or condition. Diagnostic procedures may involve X-rays, e.g. mammography for breast cancer, proctoscopy of the colon, etc.

Additionally, once a pathological state has been found to exist in the mammal and has been qualified as to the specific pathological state, there may be remedial procedures to reduce the impact of the pathologic state on the mammal, e.g. drug, radiation therapy, chemotherapy, and the like protocol, or alternately to eliminate the pathological state, e.g. by surgical procedure. In any event, the effectiveness of the remedial procedure is difficult to timely assess. For example, in the surgical removal of cancerous growth, only subsequent biopsies of proximate tissue may demonstrate total removal, and then, not necessarily on a 100 percent certain basis, let alone the possibility of metastasis.

Tests have been developed to determine the immune function of monocytes, neutrophils, lymphocytes, etc. wherein the individuality is isolated and tested for individual functionality by diverse methods. Such procedures are costly and time consuming and are not specific to a particular pathological state. Also, the results of individuality tests are difficult to interpret, let alone correlate. For example, although mammography may delineate the size, location, etc. of a lump in the breast in a female, the results will not always qualify whether the lump is cancerous or benign. Such pathological evaluation is effected by pathological observation of the actual cellular structure after biopsy or surgical removal of the lump.

Some of the above tests or procedures performed in a clinical laboratory are useful in the monitoring of certain diseases, e.g. liver enzymes for liver disease, blood urea nitrogen for kidney disease, T-cell function for immunological disorders, prothrombin and partial thromboplastin times for bleeding disorders, etc. However, such tests cannot determine either the effects of therapy on the coagulation changes in thrombotic diseases, or similar effects of therapy in cancer and other diseases which involve alterations in the immune response system.

OBJECTS OF THE INVENTION

An object of the present invention is to provide a method for determining whether a pathologic state or condition exists in a mammal.

A further object of the present invention is to provide a method for determining whether a pathological state or condition exists in mammal that may be performed in a facile and inexpensive manner.

Another object of the present invention is to provide a method for determining whether a pathological state or conditions exists in a mammal, that may be readily effected in a relatively short period of time.

Yet another object of the present invention is to provide a dependable method for determining whether a pathological state or condition exists in a mammal with minimal, if any, false readings.

A still further object of the present invention is to provide a simple method for sequentially determining the course of a known pathological state or condition in a mammal.

Still yet another object of the present invention is to provide a method for determining effectiveness of a surgical procedure on a mammal to erradicate a pathological state or condition, or to detect recurrent disease.

Another object of the present invention is to monitor the effectiveness of a drug regime or like protocol on a mammal having a known pathological state or condition.

Still another object of the present invention is to monitor the effectiveness of a remedial program for retarding growth, reducing or destroying a known pathological state or condition in a mammal.

SUMMARY OF THE INVENTION

These and other objects of the present invention are achieved by admixing an immunomodulator as defined herein and a cellular hematologic fluid of a mammal and determining a reaction parameter thereof and comparing such reaction parameter with known reaction parameters of cellular hematologic fluids of mammals of known healthy states with like immunomodulator. In a preferred embodiment of the present invention, the reaction parameter is a clotting parameter as determined as fibrin levels or a function of a time differential between fibrin levels.

In another embodiment of the present invention, the ratio between the reaction parameters of such a cellular hematologic fluid of a mammal being tested without and with an immunomodulator is compared with the ratio between the reaction parameters of cellular hematologic fluids of mammals of known healthy states without and with a like immunomodulator to assess the existence or non-existence of a pathological state or condition in the mammal being tested.

DETAILED DESCRIPTION OF THE INVENTION

It has unexpectedly been observed that a reaction parameter of a cellular hematologic fluid of a mammal with a pre-existing pathological condition when admixed with an immunomodulator is different than the reaction parameters of cellular hematologic fluids of mammals, in known healthy states when admixed with the same immunomodulator. Generally, the method of the present invention does not diagnose a specific pathological condition, but points to the existence of a pathological condition in the mammal being evaluated, although in certain instances the process of the present invention may be capable of diagnosing algorithmically a specific pathological condition. As used herein, cellular hematologic fluid of a mammal is the whole blood thereof or a fraction thereof including monocytes and other cellular or noncellular components of the mammal.

While the theory of the invention is not fully understood, nor do Applicants wish to be held to any theory of invention, it is believed that blood coagulation and/or the immune response system of a mammal having an existing pathological state or condition to an immunomodulator is different than the blood coagulation and/or immune response system of healthy mammals to like immunomodulators. While monocytes to varying degrees are involved in the immune response system of the hematologic fluid to the immunomodulator, it is believed that the immune response system involves an interreaction between the monocytes and other components, e.g. T-cells, lymphocytes, neutrophils, etc. in the cellular hematologic fluid.

The pathological conditions, the nonspecific existence of which are identified by the present invention include cancer, sepsis, AIDS, diabetes, multiple sclerosis, acute myocardial infarction, trauma, vascular thrombosis, etc. and any pathological state or condition affecting the immune response system of a mammal, it being understood by one skilled in the art that the specific pathological state or condition existing in a test mammal is generally qualified after a positive determination of the existence of a pathological state or condition in accordance with the method of the present invention. The term "mammals" as used herein includes homo sapiens, and domesticated animals, e.g. race horses.

As used herein, the term "immunomodulator" means an immunoactivator or immunoattenuator which is an agent that either promotes or accelerates, or retards or attenuates, respectively, coagulation of whole blood or whole fractions (i.e. as expressed by recalcification time (RT)). Immunomodulators include, inter alia, endotoxins, measles virus, Interferon, phorbol esters, collagens, anticoagulants such as warfarin, platelet activating factors, carrageenans, adjunct peptides, thromboplastins, antigens, myeline, gram negative bacteria, lectins such as Concanavalin-A, mitogens such as pokeweed mitogens, etc.

While there exists a plethora of reaction parameters that may be evaluated in the method of the present invention, it has been found that the clotting parameter as determined by fibrin formation, hereinafter referred to a recalcification time (RT), is a particularly facile and inexpensive method for evaluating a response of a cellular hematologic fluid to an immunomodulator. The term "recalcification time (RT)" is defined as any time period between initiation of fibrin formation to an end point thereof or to some intermediate point, it being understood that values for clotting parameters may be based on the rate of fibrin formation, for example, as defined by the integrated area beneath a rate curve between limits, etc.

Anticoagulants for whole blood or fractions thereof include the citrates such as sodium citrate, the oxalates, sodium ethylenediamine tetra-acetic acid, etc., with sodium citrate being generally preferred.

As hereinabove discussed, it has been observed that there exists a difference between the reaction parameters of cellular hematologic fluids of healthy mammals to an immunomodulator, compared to reaction parameters of cellular hematologic fluid of a mammal having a pre-existing pathological condition to such an immunomodulator. Thus, in the context of clotting parameters, and specifically recalcification times, a comparison thereof readily identifies a mammal having an existing pathological condition. Many algorithms may be developed using such reaction parameters, and more specific algorithms may be derived to more fully evaluate clotting parameters to determine the existence in a mammal of a specific pathological condition or state.

A more sophisticated algorithm is based upon the calculation of a "Thrombotic Index", defined as the ratio of the recalcification time ($RT_v$) of the cellular hematologic fluid of a mammal (in a vehicle, e.g. saline) in the absence of an immunomodulator, to the recalcification time ($RT_i$) thereof also in a vehicle and in the presence of an immunomodulator, in accordance with the following equation (I):

$$TI = RT_v \div RT_i$$

with the thrombotic index of the mammal being tested being compared with the thrombotic indices of healthy mammals.

Still another algorithm is formulated by a percent difference of clotting (PDOC) in accordance with the following equation (II):

$$PDOC = \frac{RT_v - RT_i}{RT_v} \times 100$$

The percent differences of clotting of test mammals are then compared with percent differences of clotting of healthy mammals.

There are many apparatuses available for measuring reaction parameters, e.g. chromatographic columns for concentrations of a specific chemical, as well as for measuring clotting parameters. For example, a SONO-CLOT ™ Coagulation Analyzer is available from Sienco, Inc. for measuring viscoelastic properties as a function of mechanical impedance of the sample being tested. Such analysis is very sensitive to fibrin formation thereby providing improved sensitivity and reproducibiltiy of results. There is another device, the Thromboelastograph (TEG) for similarly measuring viscoelastic properties, however the TEG is not as sensitive as the SONOCLOT® and presents disposal and cleaning problems. Still another apparatus is the HEMOCHRON® 400 available from the International Technidyne Corporation of Edison, New Jersey, evidencing significant data correlation to that of the SONOCLOT®.

To facilitate an understanding of the present invention, the following description thereof will initially be particularized with reference to the use of an endotoxin, specifically E. coli endotoxin (strain 055:B5) as the immunomodulator in a suitable vehicle, e.g. saline, on the recalcification time-endotoxin ($RT_i$) of cellular hematological fluids.

TESTING PROTOCOL

From a mammal to be tested, there is withdrawn a hematological sample, e.g. by venipuncture using a syringe (20 gauge needle) without stasis or undue force to draw blood. It will be appreciated by one skilled in the art that traumatization of blood sampling should be minimal since imperfect sampling introduces tissue factors into the blood sample and thus would impact on the validity of the results. The hematological fluid is transferred to a tube including and admixed with an anticoagulant, e.g. 3.8% solution of buffered sodium citrate. Generally, the volumetric ratio is from about nine (9) parts hematological fluid to one (1) part anticoagulant. While many anticoagulants are available, sodium citrate is generally preferred since the pH level thereof is essentially similar to the pH level of the hematological fluid of the mammal being tested, and is less toxic to the cellular elements.

Thereafter, an aliquot portion (2 milliliters) of the anticoagulated hematological fluid or citrated while blood (CWB) is admixed in a tube with the endotoxin (e.g. 20 $\mu l$ of a 1 mg/cc suspension of solution of E. coli endotoxin) and incubated for a predetermined time period, generally of from 2 to 4 hours. It has been generally found that longer incubation time periods provide result of greater sensitivity.

Generally, incubation temperatures range from about 35° C. to 40° C., preferably about 37° C. After incubation, a predetermined amount of a calcium-ion containing composition, such as calcium chloride ($CaCl_2$), e.g. 10 $\mu l$ of 0.5M $CaCl_2$ is admixed with 0.4 cc of the incubated hematologic fluid with the admixture introduced into a cuvette for insertion into the hereinabove mentioned SONOCLOT® Coagulation Analyzer [100 $\mu l$ of 0.1M $CaCl_2$ to 0.5 cc for a HEMOCHRON® 400] set to determine a recalcification time between initial fibrin formation and a "given" fibrin concentration, e.g. a 10% scale deflection as taken as an end point. If a thromboelastograph is used, the recalcification time is in terms of "R" valves. It is understood by one skilled in the art that calcium ions are necessary to initiate fibrin formation.

Recalcification Times-Immunomodulator ($RT_i$) —Mammals in Healthy State

Recalcification times-immunomodulator ($RT_i$) of a cellular hematological fluid for mammals in a healthy state range between 3.93 to 6.04 with a mean recalcification time being 4.66, as determined by TEG; and 4.6 to 7.2 with a mean of 5.69, as determined by SONOCLOT®.

Recalcification Times-Immunomodulator ($RT_i$) —Mammals With a Pathological Condition Recalcification times-immunomodulator ($RT_i$) of a cellular hematological fluid for a mammal having a pathological condition, as subsequently confirmed by other diagnostic procedures, range above or below the $RT_i$ values of healthy mammals, as more fully hereinafter disclosed and discussed.

EVALUATING PROTOCOL

Comparison of the recalcification times-immunomodulator ($RT_i$) of the cellular hematologic fluid of a test mammal with known recalcification times of cellular hematological fluids of healthy mammals permits an essentially instantaneous evaluation of the state of the test mammal, i.e. healthy or the existence of a pathological condition in the test mammal, as more fully hereinafter discussed with reference to the Examples.

Statistical analysis is used to gather and summarize data in order to make such data comprehensible and to be able to draw appropriate conclusions from the results. Discussion of the following Examples includes certain statistical analyses for a better understanding of the inventive contribution hereof. As used herein, the term "statistically significant differences between the groups studied" means that when using the appropriate statistical analysis (e.g. Chi-square tests, t-test) the probability of the groups being the same is less than 5%, e.g. $p < :0.5$. In other words, the probability of obtaining the same results on a completely random basis is less than 5 out of 100 attempts.

EXAMPLES OF THE INVENTION

The following Examples are illustrative of methods of the present invention, and it is understood that the scope of the invention is not to be limited thereby. Additionally, it will be understood by one skilled in the art that a particular pathological state was generally determined after a tested mammal (homo sapiens) exhibited a positive response to a method of the present invention. Additionally, the data with respect to healthy mammals as to a select immunomodulator at given limits to obtain recalcification times-saline ($RT_v$) and recalcification times-endotoxin ($RT_i$) established a base or standard from which the mammals being tested were generally compared for recalcification times-endotoxin ($RT_i$), thrombotic index and percent of different of clotting.

EXAMPLE I

PATHOLOGICAL CONDITION—CANCER

The normal volunteer controls were of both sexes, ranged in age from 21 to 69, and were both smokers and non-smokers. No data was ascertained from the volunteers as to current drug intake nor whether the volunteers were currently under treatment for any disease.

The following Table I sets forth mean values and ranges for $RT_i$, $RT_v$, TI and PDOC of a group of cancer patients and a group of healthy volunteers (control):

TABLE 1*

| GROUP | $RT_i$ | range | $RT_v$ | range | TI | range | PDOC | range |
|---|---|---|---|---|---|---|---|---|
| Control (n = 23) | 4.66 | 3.93–6.04 | 6.13 | 5.24–7.61 | 1.32 | 1.15–1.53 | 23.4 | 14.0–34.5 |
| Cancer (n = 25) | 2.25 | 1.54–4.02 | 6.46 | 4.45–8.72 | 2.71 | 1.62–4.39 | 60.3 | 38.3–88.0 |
|  | $p < 0.001$ | | $p = NS$ | | | | | |

*Recalcification times determined by TEG.

The cancer patients were evaluated at the time of diagnosis of the disease. There were significant differences between the recalcification times-endotoxin ($RT_i$) between the group of the healthy volunteers and the group of the cancer patients, whereas there were no significant differences between recalcification times-saline ($RT_v$) of such groups. Additionally, it can be readily seen that the thrombotic index (TI) is greater for the group of cancer patients than the thrombotic index (TI) of the healthy volunteers. The same proposition held true of the comparison of percent difference in clotting (PDOC) therebetween. The values for TI or PDOC do not overlap for these groups.

It has been found in cancer patients where a large portion of the tumor load is removed and minute portions remain, that the $RT_i$, TI and PDOC differences still range outside the parameters of the group of healthy volunteers. A patient having cancer of the colon exhibited TI and PDOC values of 1.91 and 47.6%, respectively, one week post surgery. It was subsequently determined that tumor growth had invaded adjoining tissue.

The method of the present invention permits a clinician to evaluate effects of therapy on the state of the cancer in a cancer patient. For example, small changes in $RT_i$ values and a lowering of TI or PDOC values after non-fully curative treatments have been demonstrated. If chemotherapy and/or radiation treatment do not alter such values, changes in the treatment are then suggested to find a more effective drug regime and/or radiation protocol. An advantage of the method of the present invention is the convenience of sampling and evaluation at varying times after therapy and the assessment of effectiveness of treatment prior to physical appearance of clinical changes.

Of the types of cancers detected by the method of the present invention included are cancers of the lung, breast, biliary tract, bladder, larynx, ovary, head and neck, colon, rectum, esophagus, soft palate, pancreas, and floor of the mouth. As hereinabove mentioned, the presence or absence of remaining malignancy after curative surgery may be determined by the methods of the present invention.

EXAMPLE II

PATHOLOGICAL CONDITION—BREAST CANCER

The following Table II sets forth specific data with reference to six patients; patients 1 to 4 having cancer and patients 5 and 6 having benign breast lesions.

TABLE II*

| Patient | $RT_i$ | $RT_v$ | TI | PDOC |
|---|---|---|---|---|
| 1 | 2.00 | 7.31 | 3.66 | 72.6 |
| 2 | 3.28 | 7.04 | 2.15 | 53.4 |
| 3 | 2.51 | 6.61 | 2.63 | 60.2 |
| 4 | 3.52 | 6.06 | 1.72 | 42.0 |
| 5 | 4.32 | 4.54 | 1.05 | 4.84 |
| 6 | 4.87 | 5.98 | 1.23 | 18.6 |

*Recalcification times determined by TEG.

The above date clearly illustrates a lower recalcification times-endotoxin ($RT_i$) for the patients (#1–#4) with breast cancer as distinguished from the patients (#5–#6) with benign breast lesions. A similarity of comparison was noted between the $RT_i$ values of patients (#1–#4) and $RT_i$ values set forth in Table I, above. Additionally patients (#1–#4) had significantly higher TI and PDOC values.

Patients #3 and #4, post one week surgery, exhibited TI and PDOC values of 1.25 and 1.39 and 20.0% and 27.9%, respectively, indicative of the successful removal of all malignance as demonstrated by subsequent histological examination of tissue and non-existence of cancerous cells in the lymph nodes.

As hereinabove discussed, in cancer cases where the malignancy is not totally removed, the $RT_i$, TI and PDOC values remain in the pre-operative ranges.

EXAMPLE III

PATHOLOGICAL CONDITION—DIABETES

The following Table III sets forth mean values for $RT_i$ and $RT_v$ of a group of 36 patients having diabetes:

TABLE III*

| Group | $RT_i$ | Range | $RT_v$ | Range |
|---|---|---|---|---|
| Control 5.3–8.5 (n = 19) | 5.69 ± 0.74 | 4.6–7.2 | 6.55 ± 0.08 | |
| Diabetics | 4.99 ± 1.20 $p < 0.001$ | 3.0–8.1 | 5.65 ± 2.3 $p < 0.001$ | 3.3–16.8 |

*Recalcification times determined by SONOCLOT ® Coagulation Analyzer.

Eighteen of 36 (50%) diabetics had accelerated clotting in the saline incubated samples and 15 of 36 (42%) had clotting times shorter than the shortest control value for the endotoxin incubated samples. It would appear that diabetics with abnormal values have the more severe disease (e.g. juvenile diabetics, diabetics with vascular complications, diabetics with disease more than 15 years, etc.). The methods of the present invention will be useful in measuring therapeutic effects on diabetic activity, such as diet control, exercise and drug treatment, and may become a goal of the therapy to bring the $RT_v$ and $RT_i$ values of diabetics into the normal range.

EXAMPLE IV

PATHOLOGICAL CONDITION—ACQUIRED IMMUNE DEFICIENCY SYNDROME (AIDS)

The following Table IV sets forth mean values and ranges of $RT_i$, $RT_v$, TI and PDOC of healthy volunteers (per Example I) with mean values and ranges of $RT_i$, $RT_v$, TI and PDOC of four (4) confirmed advanced AIDS patients:

TABLE IV*

| Group | $RT_i$ | range | $RT_v$ | range | TI, | range | PDOC, | range |
|---|---|---|---|---|---|---|---|---|
| AIDS | 4.94 | 4.43–5.40 | 5.78 | 5.12–6.94 | 1.17 | 1.08–1.29 | 14.5 | 7.5–22.2 |
| Control | 4.66 | 3.93–6.04 | 6.13 | 5.24–7.61 | 1.32 | 1.15–1.53 | 23.4 | 14.0–34.5 |

*Recalcification time determined by TEG.

From the above data, it can be seen that an evaluation of the recalcification times-endotoxin ($RT_i$) of the AIDS patients are higher, but not necessarily significant as distinguished from like comparison of cancer patients. It is noted, however, that the TI and PDOC values are significantly lower, particularly in three out of four cases. Another form of algorithm could be derived to more unequivocally identify all such AIDS patients. Thus, the methods of the present invention illustrate that mammals having AIDS or AIDS-like disease have a PDOC value below the control, and with some statistically determined base line value, to qualify individuals for blood donation.

EXAMPLE V

PATHOLOGICAL CONDITION—SEPSIS, TRAUMA, AND/OR SURGERY PATIENTS

In surgical intensive care units, particularly patients exposed to sever trauma and/or major surgery and are being managed by life-support systems frequently succumb to multi-system failure resulting from progressive and perhaps undetected sepsis.

The following Table V sets forth values of group (9 patients) exhibiting a localized septic condition from a group (62 patients) who did not exhibit such a condition, it being noted that $RT_i$ values are lower and TI and PDOC values are higher, as expected (compared to a normal population) as a result of released thromboplastins and immunological consequences from the presence of traumatized tissues:

TABLE V*

| GROUP | $RT_i$ | $RT_v$ | TI | PDOC |
|---|---|---|---|---|
| Control | 4.66 | 6.53 | 1.32 | 23.4 |
| Septic | | | 8 < 1.30 > 2 | 8 < 23.0 > 2 |
| Non-Septic | | | 2 < 1.30 > 60 | 2 < 23.0 > 60 |
| | | | p < 0.001 | |

*Recalcification times determined by TEG.

As hereinabove mentioned, as a result of the traumatic condition of the patients being tested, the $RT_i$, and TI values are not readily comparable with values of $RT_i$ and TI of non-surgery of pre-surgery patients.

In eighty percent (80%) of the septic patients, the thrombotic indices are not elevated, as expected. Values of TI lower than 1.30 and PDOC values lower than 23.0% usually shown the presence of sepsis in the abdominal cavity of the patient, probably due to the fact that high concentrations of an immunomodulator have entered the bloodstream of such individuals.

EXAMPLE VI

PATHOLOGICAL CONDITION—IMMUNOCOMPETENCE

The following Table VI sets forth the $Rt_i$, $RT_v$, TI and PDOC values for post-operative and post-traumatic patients for non-surviving patients (9), surviving patients (46), and non-operative normal volunteers (23):

TABLE VI*

| Group | $RT_i$ | $RT_v$ | TI | PDOC |
|---|---|---|---|---|
| Control | 4.66 | 6.53 | 1.32 | 23.4 |
| Non-Survivor | 4.51 | 6.72 | 1.49 | 32.9 |
| Survivor | 2.21 | 6.09 | 2.75 | 63.9 |

*Recalcification times determined by TEG.

There were no significant differences in the $RT_v$ values, but highly significant differences in the $RT_i$, TI, and PDOC values between survivors and non-survivors. Unlike the elevated value of TI and PDOC in cancer patients, elevated values occurring within 48 hours post-operative or post-trauma patients are good prognostication indicators. If the post-operative values are low, there is an indication of possible septic complications. Further, a TI value of 1.60 appears to be the threshold value of immunocompetence, since 8 of 9 patients who died had values below 1.60, whereas only one patient with a value above 1.60 died.

The test measures the immunocompetence of an individual. Therefore, activation (accelerated clotting) in response to test endotoxin, of the cancer patient (early diagnosed), and post-operative or post-trauma patients, each showing an altered (activated) state of the immune response system as reflected in accelerated clotting time under the influence of test endotoxin, may in part explain the thrombotic complications associated with these states.

EXAMPLE VII

PATHOLOGICAL CONDITION—MULTIPLE SCLEROSIS

The following Table VII sets forth values of 33 patients with multiple sclerosis, many of whom were in clinical remission at the time of testing:

TABLE VII*

| Group | $RT_i$ | Range | $RT_v$ | Range | PDOC |
|---|---|---|---|---|---|
| MS Patients (n = 33) | 3.67 ± 1.27 | 1.2–7.0 | 4.99 ± .93 | 2.7–7.3 | 26.2 ± 20.0 |
| Control (n = 19) | 5.69 ± .75 | 4.6–7.2 | 6.55 ± .82 | 5.3–8.5 | 12.2 ± 11.1 |

*Recalcification times determined by SONOCLOT ® Coagulation Analyzer

Twenty-two of the 33 MS patients exhibited abnormal $RT_v$ values, and 29 of the 33 patients had abnormal $RT_i$ values. The data indicates that an active disease state is present, even though a state of clinical remission is observed. It is readily appreciated by one skilled in the art that a practitioner will utilize the methods of the present invention to tailor medical therapy to the presence of an active disease, as well as to monitor the patient's condition during therapy.

As indicated earlier and as illustrated above, the test method of this invention is capable of detecting a variety of disease states in which the latent procoagulant generation is elevated (activated monocytes). These states include myocardial infarction, stroke, infections, acquired immune dysfunction syndrome (AIDS), rheumatoid arthritis, cancer, multiple sclerosis, etc.

In addition, by varying the concentrations of the immunomodulators, e.g., endotoxin, carrageenan, etc., the sensitivity to a threshold challenge can be ascertained. In some states cancer, multiple sclerosis, etc., use of immunomodulator concentrations one-hundredth the optimum concentration can also detect an activated cell in a blood sample. Use of these varying immunomodulator does concentrations enables the detection, and effects of therapy on some diseases.

There are a variety of immunomodulators than can activate isolated monocytes and thereby stimulate these cells to generate a procoagoulant activity in culture. These stimulants include endotoxin, immune complexes, complement split products, inflammatory particles, amines, phorbol esters, lectins, antigens, chemical mediators of inflammation, lipoproteins, virus damaged cells, tumor cells, etc. It is believed that the stimuli that activate monocytes interact with cellular plasma membranes. Perturbation of these membranes can occur via immunomodulatory-cell membrane contact involving specific receptors or unspecific interactions.

from individuals with a variety of disease states. In some examples, differences can be seen in the values obtained between saline, endotoxin and other immunomodulators but they may not be significant (p values) changes. This is due to the relatively small sample size and/or the fact that bloods from healthy and varying disease states were utilized.

In Table VIII, below, the number of citrated whole blood samples tested, the mean RT saline $\pm$SD (standard deviation of the means) RT endotoxin $\pm$SD and RT immunomodulator $\pm$SD are tabulated. The analysis of variance (ANOVA) was used when comparing the means for the different group values of P-0.05 are significant.

TABLE VIII

| Number of Samples | Concentration | Saline | Endotoxin | Immunomodulator | Catagory |
|---|---|---|---|---|---|
| 3 | 10 μg/cc | 6.43 ± 1.70 | 5.00 ± .85 | 5.23 ± .68<br>Adjunct Peptide | Adjunct peptide, muamyl peptide immunological activator, 10 μg/cc CWB |
| 9 | 20 μg/cc | 6.97 ± 1.94 | 5.29 ± .93* | 5.36 ± 1.51<br>Con A | Lectin |
| 9 | 20 μg/cc | 4.90 ± 1.28 | 4.57 ± 1.07 | 4.57 ± 1.32<br>Pokeweed | Mitogen |
| 9 | unknown | 4.90 ± 1.28 | 4.57 ± 1.07 | 4.79 ± 1.03<br>Virus | Measles virus |
| 7 | 2 μg/cc | 5.30 ± .91 | 4.09 ± .57* | 5.30 ± 1.04<br>PAF | Platelet activating factor, lipid, mediator released during trauma and inflammation, allergy |
| 5 | 20 μg/cc | 6.04 ± 1.26 | 5.22 ± .49 | 4.54 ± .45**<br>Zymosan | Zymosan - immunomodulator |
| 7 | 1 μg/cc | 5.51 ± .74 | 5.94 ± .63 | 5.10 ± .87<br>Myelin | Myelin, protein, antigen |

| Number of Samples | Final Concentration | RT Saline ± SD | RT Endotoxin ± SD | RT Immunomodulator ± SD | Catagory |
|---|---|---|---|---|---|
| 5 | 1 μg/cc | .56 ± 1.33 | 5.10 ± 1.92 | 5.86 ± 1.34<br>TPA | 12-O—tetradecanoyl phorbol 13-acetate (TPA phorbal ester) cellular activator |
| 3 | .001 unit/cc | 4.37 ± .76 | 3.50 ± 2.35 | 3.56 ± 0.72<br>Thrombin | Thrombin - enzyme procoagulant |
| 7 | 2.0 units/cc | 4.91 ± .51 | 4.13 ± 1.08* | 3.72 ± 1.27**<br>Interferon | Interferon - immunologicalmediator pharmacological agent |
| 9 | 10 μg/cc | 4.80 ± 1.14 | 4.22 ± 0.84* | 3.28 ± 0.68**<br>Carrageenan | Carrageenan - inflammatory mediator, colloid |
| 9 | 400 μg/cc | 4.80 ± 1.14 | 4.22 ± 0.84* | 3.55 ± .72**<br>Latex Beads | Latex Beads, phagocytic particle |
| 8 | 10 μg/cc | 5.26 ± 1.58 | 3.04 ± 1.20* | 4.35 ± 1.70**<br>Collagen | Platelet activator, abnormal surface for blood contact, immonomodulator |
| 5 | 3.0 mg/cc | 5.18 ± .88 | 4.26 ± .78* | 6.62 ± 1.62<br>ammonium chloride | Amine, intracellular compartment modifier affects pH. |

*signifies RT endotoxin different than RT saline.
**signifies RT immunomodulator different than RT saline.

EXAMPLE VIII

COMPARATIVE TESTS WITH ADDITIONAL IMMUNOMODULATORS

The purpose of these examples is to show that a multitude of immunomodulators in this protocol in which whole blood is employed can be utilized and that endotoxin was just a representative of the group.

The citrated blood samples utilized to obtain the following data were form normal individuals as well as In addition to the above immunomodulators, the following materials were successfully on at least one sample:

| NAME | CATEGORY |
|---|---|
| Lipid A | lipid, bacterial product |
| Ionophore A 23187 | pharmacological stimulant |
| Mixed Bloods | foreign cells, complement, immune complex formation etc. |
| Cycloheximide | DNA, RNA inhibitors, antibiotic |
| Snake Venom | immunologically active, procoagulant |
| Nicotine | Vasoactive biochemical |
| Salmonella & Other Endotoxins | bacterial products |
| Adenosine Diphosphate | effects cellular energy balance platelet aggregation |
| Mixed Plasma | foreign species |

-continued

| NAME | CATEGORY |
|---|---|
| Tuftsin | tetrapeptide - leukocyte stimulant |
| Glucan | yeast cell wall, foreign surface |
| Streptokinase | clot dissolving agent, lyte agent, immunologically active |
| Urokinase | clot dissolving agent, lyte agent, immunologically active |
| Papain | enzyme |
| Immunoglobulin G (IgG) | inflammatory blood product |
| Ferritin | foreign protein |
| PPD | purified protein derivative |
| Phytohemagluttinin | lectin |
| Pathophysiological Agents | damaged cells, etc. |

EXAMPLE IX

In this Example, the effect of varying immunomodulator concentrations on recalcification times was measured. The immunomodulators, and other parameters of testing are set forth below:

A. Thromboplastin, (also called tissue factor of clotting factor III). Material generated by monocytes, procoagulant, immunomodulator.

| Concentration of tissue factor (ug/cc CWB) | | | |
|---|---|---|---|
| 0 | 3 | 6 | 15 |
| RT ± SD  6.11 ± 0.92 | 2.98 ± .60 | 2.34 ± .35 | 1.96 ± .51 | n = 8 samples

Significance ANOVA $p < .05$ for comparisons between different groups.

B. *E. coli* endotoxin

| Concentration of endotoxin (ug/cc CWB) | | | |
|---|---|---|---|
| 0 (A) | 10 (B) | 1.0 (C) | 0.1 (D) |
| RT ± DF  5.25 ± 1.03 | 3.75 ± .78 | 4.20 ± .49 | 4.16 ± .32 | n = 8 samples
Significance (ANUA)
A vs B; $P < .001$
A vs C; $P < .05$
A vs D; $P < .05$
B vs C; $P = NS$
C vs D; $P = NS$ By varying immunomodulator concentrations, the threshold quantity necessary to give a significant change in RT relative to that of the saline value may be of clinical significance. The minimum concentration of a particular immunomodulator necessary to produce change is called threshold value and this may vary between diseases and may enable a differential diagnosis (e.g. cancer, not diabetes, etc.) to be made.

EXAMPLE X

USE OF TEST IN MONITORING DRUG THERAPY

Samples of citrated whole blood from patients (4) on Warfarin (anticoagulant) therapy were analyzed with this test. The prothrobin time of patients ranged between 18.6 to 65 seconds (normal 12 sec.).

| RT saline (min) | RT endotoxin (min) |
|---|---|
| 18.7 ± 3.56 | 5.48 ± 2.91 | significance, paired t test, $P < .02$

The RT saline is very prolonged due to the anticoagulant drug. However, RT endotoxin mean is in the normal range suggesting that this anticoagulant has little effect on tissue factor generation.

Advantages of the present invention are many, e.g. donor blood may be pre-screened, particularly where a pathological condition of AIDS may exist, let alone the undesirability of use of blood for transfusions where such blood evidences the existence of a pathological state or condition in the blood donor. The present invention may be used to evaluate compatibility of transfusion of a particular blood donor. Still further, the methods of the present invention permit the facile monitoring of the effectiveness of drug therapy or regime to a particular pathological condition or state in a mammal, e.g. diabetes. The present invention permits a facile evaluation of the potential acceptance or rejection by a mammal of a transplant organ.

While the present invention is discussed with primary reference to the evaluation of a cellular hematologic fluid to determine if a mammal has a pre-existing pathological condition, it is apparent to one skilled in the art that the method of the present invention may be used in the prognosis of treatment of a known pathogenic state in a mammal. A illustrated, in Example II above, the immune response system of the cellular hematologic fluid of a mammal having undergone surgery for the removal of cancerous tissue may be evaluated to determine if all cancerous tissue has been removed from the mammal and/or the extent of sepsis thereof. Similarly, a post-operative protocol, e.g. chemotherapy, may be monitored for effectiveness of such post-operative protocol.

While the invention herein has been described in connection with exemplary embodiments thereof, it will be understood that many modifications will be apparent to those of ordinary skill in the art and that this application is intended to cover any adaptations or variations thereof. Therefore, it is manifestly intended that this invention be only limited to the claims and the equivalents thereof.

What is claimed is:

1. A method for analyzing the blood of a mammal to determine the presence or development of pathology suspected of causing abnormalities in the immune response system and/or the blood coagulation of the mammal consisting essentially of:

A. preparing a quantity of anticoagulated whole blood from a sample of whole blood taken from;
   B. taking an aliquot portion of said anticoagulated blood and introducing said aliquot portion into a first container having therein a vehicle, and thereby preparing a control sample;
   C. taking a further aliquot portion of said anticoagulated blood and introducing said further aliquot portion into a second container having therein immunomodulator and a vehicle and thereby preparing an activated sample;
   D. incubating said control sample and said activated sample at a predetermined suitable incubation temperature from about 1 to about 4 hours;
   E. initiating clotting activity and measuring a reaction parameter for each of said control sample and said activated sample; and
   F. identifying the presence of pathology by comparing the reaction parameters measured in Step E with similar reaction parameters measured from a mammal in a healthy state.

2. The method of claim 1, wherein said anticoagulated blood is prepared by mixing a sample of the blood taken from said mammal with an anticoagulant selected from the group consisting of sodium citrate and sodium oxalate.

3. The method of claim 1, wherein said immunomodulator is present in an amount of about 20 ug/cc of a mg/cc solution or suspension of citrated whole blood.

4. The method of claim 1, wherein said suitable vehicles comprise a quantity of physiological saline solution.

5. The method of claim 1, wherein said mammal is a homo sapien.

6. The method of claim 1, wherein said immunomodulator is selected from the group consisting of endotoxins, virus, Interferon, phorbol esters, collagens, anticoagulants platelet activating factors, carrageenans, adjunct peptides thromboplastins, antigens, myelin, gram negative bacteria, lectins and mitogens.

7. The method of claim 6, wherein said immunomodulator is an endotoxin.

8. The method of claim 1 wherein said predetermined temperature ranges from about 35° C. to about 40° C.

9. The method of claim 8, wherein said predetermined temperature is approximately 37° C.

10. A method for monitoring the current status of a pathological state in a mammal, comprising:
K. analyzing the blood of said mammal wherein said pathological state is present in accordance with the method of claim 1, to determine the reaction parameters for said known pathological state;
L. analyzing a further sample of the blood of said mammal at a predetermined time interval also in accordance with the method of claim 1, to determine the reaction parameters thereof; and
M. comparing the reaction parameters of Steps K and L to determine said current status in said mammal.

11. The method of claim 10, wherein the comparison of Step M is performed by:
Q. determining the Thrombotic Index (TI) of said mammal's blood derived from the respective reaction parameters gathered from each of Steps K and L, said Thrombotic Index comprising the ratio of the recalcification time of said control sample ($RT_v$) to the recalcification time of said activated sample (RTi), (RI=RTv/RTi); and
R. comparing the Thrombotic Index derived from the reaction parameters of Step K with the Thrombotic Index derived from the reaction parameters of Step L.

12. The method of 10, wherein the comparison of Step M is performed by:
S. determining the Percentage Difference of Clotting (PDOC) of said mammal's blood derived from the respective reaction parameters gathered from each of Steps K and L, said PDOC comprising the difference between the recalcification times of said control sample (RTv) and said activated sample (RTi), said difference multiplied by 100 and divided by the said control sample recalcification time.
PDOC (RTv−RTI)×100÷RTv; and
T. comparing the PDOC value derived from the reaction parameters of Step K with the PDOC value derived from the reaction parameters of Step L.

13. A method for assessing the effectiveness of corrective surgery on a mammal having an operative pathologic state, which comprises:
N. analyzing the blood of said mammal prior to said corrective surgery in accordance with the method of claim 1, to determine the reaction parameters thereof;
O. analyzing a further sample of the blood of said mammal taken after said corrective surgery, also in accordance with the method of claim 1, to determine the reaction parameters thereof; and
P. comparing the reaction parameters of Steps A and B to determine the effectiveness of said corrective surgery.

14. The method of claim 13, wherein the comparison of Step P is performed by:
Q. determining the Thrombotic Index (TI) of said mammal's blood derived from the respective reaction parameters gathered from each of Steps N and O, said Thrombotic Index comprising the ratio of the recalcification time of said control sample (RTv) to the recalcification time of said activated sample (RTi), (TI=RTv/RTi); and
R. comparing the Thrombotic Index derived from the reaction parameters of Step N with the Thrombotic Index derived from the reaction parameters of Step O.

15. The method of claim 13, wherein the comparison of Step P is performed by:
S. determining the Percentage Difference of Clotting (PDOC) of said mammal's blood derived from the respective reaction parameters gathered from each of Steps N and O, said PDOC comprising the difference between the recalcification times of said control sample (RTv) and said activated sample (RTi), said difference multiplied by 100 and divided by the said control sample recalcification time,
PDOC (RTv−RTI)×100÷RTv; and
T. comparing the PDOC value derived from the reaction parameters of Step N with the PDOC value derived from the reaction parameters of Step O.

16. The method of claim 1, wherein said reaction parameters are clotting parameters thereof.

17. The method of claim 16, wherein said clotting parameters are recalcification times as determined by fibrin formation.

18. The method of claim 17, wherein clotting activity in Step E is initiated by adding to the samples a compound containing calcium ions.

19. The method of claim 17, wherein the comparison of Step F is performed by:
G. determining the Thrombotic Index (TI) of said mammal's blood, comprising the ratio of the recalcification time of said control sample ($RT_v$) to the recalcification time of said activated sample ($RT_i$), (RI=$RT_v$/$RT_i$); and
H. comparing the Thrombotic Index determined in Step A with one or more Thrombotic Indices previously determined from ratios derived from the recalcification times of standard control samples and corresponding activated samples derived from healthy mammals.

20. The method of claim 17, wherein the comparison of Step F is performed by:
I. determining the Percentage Difference of Clotting (PDOC) of said mammal's blood, comprising the difference between the recalcification times of said control sample ($RT_v$) and said activated sample ($RT_i$), said difference multiplied by 100 and divided by the said control sample recalcification time, $PDOC = (RT_v - RT_i) \times 100 \div RT_v$; and J. comparing the Percentage Difference of Clotting (PDOC) determined in Step A with standard PDOC values previously determined from the correlation of the recalcification times of standard control samples and corresponding activated samples derived from healthy mammals.

* * * * *